United States Patent [19]

Lantzsch et al.

[11] Patent Number: 5,621,141
[45] Date of Patent: Apr. 15, 1997

[54] PROCESS FOR THE PREPARATION OF ALKYLCARBOXYLIC ACID 4-HYDROXYANILIDES

[75] Inventors: Reinhard Lantzsch, Wuppertal; Eric Rivadeneira, Leverkusen; Werner Lindner, Cologne, all of Germany

[73] Assignee: Bayer Aktiengesellschaft, Leverkusen, Germany

[21] Appl. No.: 579,924

[22] Filed: Dec. 28, 1995

[30] Foreign Application Priority Data

Jan. 4, 1995 [DE] Germany ............ 19 50 0119.2

[51] Int. Cl.$^6$ ............................ C07C 231/02
[52] U.S. Cl. ................................ 564/142
[58] Field of Search ...................... 564/142

[56] References Cited

U.S. PATENT DOCUMENTS

| | | | |
|---|---|---|---|
| 5,059,623 | 10/1991 | Kruger et al. | 514/613 |
| 5,302,742 | 4/1994 | Landscheidt et al. | 560/29 |
| 5,492,931 | 2/1996 | Krueger et al. | 514/613 |

FOREIGN PATENT DOCUMENTS

| | | |
|---|---|---|
| 0339418 | 11/1989 | European Pat. Off. . |
| 0569792 | 11/1993 | European Pat. Off. . |
| 0608738 | 8/1994 | European Pat. Off. . |

OTHER PUBLICATIONS

F. Moller, "Houben–Weyl, Methoden der Organischen Chemie", vol. XI/2, pp. 10–14, Georg Thieme Verlag, Stuttgart, (1958).

Chemical Abstracts, vol. 92, No. 9, abstract No. 76953h, p. 2, (1980).

Chemical Abstracts, vol. 89, No. 13, abstract No. 107264d, p. 729 (1978).

*Primary Examiner*—Richard L. Raymond
*Attorney, Agent, or Firm*—Sprung Horn Kramer & Woods

[57] ABSTRACT

The Application describes a new process for the preparation of alkylcarboxylic acid 4-hydroxyanilides by reaction of aminophenols with carboxylic acid derivatives in organic solvents without the addition of a base reacts.

5 Claims, No Drawings

PROCESS FOR THE PREPARATION OF ALKYLCARBOXYLIC ACID 4-HYDROXYANILIDES

The present invention relates to a new process for the preparation of known alkylcarboxylic acid 4-hydroxyanilides.

It is already known that alkylcarboxylic acid 4-hydroxyanilides can be obtained by reaction of 4-hydroxyanilines with alkylcarboxylic acid halides (EP-A 339418). The preparation is not simple, since several by-products may be formed. If the carboxylic acid chloride reacts first with the hydroxyl group of the aminophenol, carboxylic acid phenyl esters are obtained instead of the desired carboxylic acid anilides. It is furthermore possible that the amino group of the aminophenol reacts twice with the carboxylic acid chloride, or that the hydroxyl group and the amino group of the aminophenol react with the carboxylic acid chloride at a similar rate, so that an O,N-bisacyl compound or an O,N,N-trisacyl compound is formed.

The preferred procedure in EP-A 339418 is therefore to use a tertiary amine as the auxiliary base and to carry out the reaction at temperatures between 0° C. and 20° C. Furthermore, water-miscible solvents are preferred. This procedure is associated with a large number of difficulties:

the tertiary amine present as hydrochloride in the mother liquor must be recovered expensively in an industrial process involving several process steps.

The low reaction temperature leads to very long reaction times and to the use of a considerable excess of carboxylic acid chloride, so that considerable amounts of the di- or triacylated compound are already formed.

The solvent can be recovered from the aqueous mother liquor only with increased distillation expenditure.

The aqueous mother liquor represents a considerable waste water problem from the point of view of the amount and loading.

A product of adequate purity is obtained only after recrystallization.

An improved process is described in EP-A 569792: it is carried out in a two-phase system of water and an organic solvent, and an aqueous base, such as, for example, 20% strength sodium hydroxide solution, is preferably employed as the base.

The process has the disadvantage that such two-phase systems, in which neither starting substance nor end product are soluble, are difficult to stir. Furthermore, a large amount of waste water containing chlorine compounds is obtained, and this is not biologically degradable without problems.

It has now been found that alkylcarboxylic acid 4-hydroxyanilides of the general formula (I).

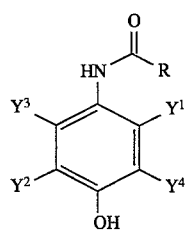

in which

R represents alkyl which is optionally mono- or polysubstituted in an identical or different manner by halogen, or represents cycloalkyl which is optionally mono- or polysubstituted in an identical or different manner by alkyl, halogenoalkyl or halogen and $Y^1$, $Y^2$, $Y^3$, $Y^4$ are identical or different and represent hydrogen, halogen, cyano, in each case optionally halogen-substituted alkyl, alkoxy or alkylthio, are obtained in a high yield and high purity, when aminophenols of the general formula (II)

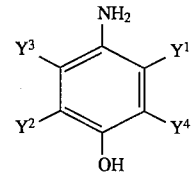

in which $Y^1$, $Y^2$, $Y^3$, $Y^4$ have the abovementioned meaning, are reacted with carboxylic acid derivatives of the general formula (III)

in which

R has the abovementioned meaning and

X represents halogen, preferably chlorine, without the addition of a base, in an organic solvent in the absence of water, at temperatures from 50° to 180° C.

In the definitions, the hydrocarbon chains, such as alkyl, including those linked by heteroatoms, as in alkoxy or alkylthio, are in each case straight-chain or branched.

Halogen in general represents fluorine, chlorine, bromine or iodine, preferably fluorine, chlorine or bromine, in particular fluorine or chlorine.

The process according to the invention has a number of advantages. The acylated aminophenols of the general formula (I) are formed in a very high yield, no waste water is formed, and the hydrogen halide liberated, preferably hydrogen chloride, escapes in gaseous form and can easily be re-used. The product purities are above 95%.

It is to be described as decidedly surprising that such good yields are achieved by the process according to the invention, since under the reaction conditions both anilines or aniline hydrochlorides (Houben-Weyl, Volume E5, page 972) react with acid chlorides, but phenols react even under very mild conditions without acid-trapping agents to give esters (Houben-Weyl, Volume E5, page 543).

It was therefore not to be expected by the expert that the preparation of the compounds of the general formula (I) would take place in a high yield and adequate purity by this method.

Compounds of the general formula (I) which are preferably prepared by the process according to the invention are those in which R represents straight-chain or branched alkyl having 1–8 carbon atoms which is optionally mono- to tetrasubstituted in an identical or different manner by halogen, or represents cyclopropyl, cyclobutyl, cyclopentyl, cyclohexyl or cycloheptyl which are in each case optionally mono- to tetrasubstituted in an identical or different manner by halogen, straight-chain or branched halogenoalkyl or alkyl having 1 to 4 carbon atoms, $Y^1$ represents hydrogen, fluorine, chlorine, bromine, cyano, straight-chain or branched alkyl having having 1 to 4 carbon atoms, or in each case straight-chain or branched alkoxy or alkylthio having in each case 1 to 4 carbon atoms, or represents in each case straight-chain or branched halogenoalkyl, halogenoalkoxy or halogenoalkylthio having 1 to 4 carbon atoms and 1 to 5 identical or different halogen atoms, $Y^2$ represents hydrogen, fluorine, chlorine, bromine, cyano, straight-chain or branched alkyl having having 1 to 4 carbon atoms, or in each case straight-chain or branched alkoxy or alkylthio having in each case 1 to 4 carbon atoms, or represents in each case straight-chain or branched halogenoalkyl, halogenoalkoxy or halogenoalkylthio having 1 to 4 carbon atoms and 1 to 5 identical or different halogen atoms, $Y^3$ represents hydrogen, fluorine, chlorine, bromine, cyano, straight-chain or branched alkyl having having 1 to 4 carbon atoms, or in each case straight-chain or branched alkoxy or alkylthio having in each case 1 to 4 carbon atoms, or represents in each case straight-chain or branched halogenoalkyl, halogenoalkoxy or halogenoalkylthio having 1 to 4 carbon atoms and 1 to 5 identical or different halogen atoms, $Y^4$ represents hydrogen, fluorine, chlorine, bromine, cyano, straight-chain or branched alkyl having having 1 to 4 carbon atoms, or in each case straight-chain or branched alkoxy or alkylthio having in each case 1 to 4 carbon atoms, or represents in each case straight-chain or branched halogenoalkyl, halogenoalkoxy or halogenoalkylthio having 1 to 4 carbon atoms and 1 to 5 identical or different halogen atoms.

Compounds of the general formula (I) which are prepared in particular by the process according to the invention are those
in which
R represents methyl, ethyl, n- or i-propyl, n-, i-, sec-, or t-butyl, 1-, 2-, 3-, tert-, or neo-pentyl, 2-methyl-1-butyl, 3-methyl-1-butyl or 3-methyl-2-butyl which are in each case optionally mono-, di- or trisubstimted in an identical or different manner by fluorine, chlorine or bromine, or represents cyclopropyl, cyclobutyl, cyclopentyl, cyclohexyl or cycloheptyl which are in each case optionally mono- or di-substituted in an identical or different manner by fluorine, chlorine, bromine, methyl, ethyl, n-propyl, i-propyl, chloromethyl, chloroethyl or trifluoromethyl, $Y^1$ represents hydrogen, fluorine, chlorine, bromine, cyano, methyl or trifluoromethyl, $Y^2$ represents hydrogen, fluorine, chlorine, bromine, cyano, methyl or trifluoromethyl, $Y^3$ represents hydrogen, fluorine, chlorine, bromine, cyano, methyl or trifluoromethyl, $Y^4$ represents hydrogen, fluorine, chlorine, bromine, cyano, methyl or trifluoromethyl.

Compounds of the general formula (I) which are especially preferably prepared by the process according to the invention are those
in which
R represents methyl, ethyl, n- or i-propyl, n-, i-, sec- or t-butyl, 1-, 2-, 3-, tert-, or neo-pentyl, 2-methyl-1-butyl, 3-methyl-1-butyl, 3-methyl-2-butyl which are in each case optionally mono-, di- or trisubstituted in an identical or different manner by fluorine, chlorine or bromine, or represents cyclopropyl, cyclobutyl, cyclopentyl, cyclohexyl or cycloheptyl which are in each case substituted in the 1-position by methyl, ethyl, chlorine, bromine or trifluoromethyl and are in each case optionally substituted by a further alkyl radical having 1, 2 or 3 carbon atoms, $Y^1$ represents hydrogen, fluorine, chlorine, bromine, cyano, methyl or trifluoromethyl, $Y^2$ represents hydrogen, fluorine, chlorine, bromine, cyano, methyl or trifluoromethyl, $Y^3$ represents hydrogen, fluorine, chlorine, bromine, cyano, methyl or trifluoromethyl, and $Y^4$ represents hydrogen, fluorine, chlorine, bromine, cyano, methyl or trifluoromethyl.

Formula (II) provides a general definition of the aminophenols required as starting substances for carrying out the process according to the invention. In this general formula (II) the radicals $Y^1$, $Y^2$, $Y^3$ and $Y^4$ preferably or in particular have those meanings which have already been mentioned above as preferred or as particularly preferred for $Y^1$, $Y^2$, $Y^3$ and $Y^4$ in connection with the description of the compounds of the general formula (I). The starting substances of the general formula (II) are known and/or can be prepared by processes which are known per se (compare Cesare Ferri, "Reaktionen in der organischen Synthese" [Reactions in organic synthesis], 1978, 81, 89, 91, 97, 118, 120, 122, 124, 126, 128; EP-A 339418).

Formula (III) provides a general definition of the alkyl carboxylic acid derivatives furthermore required as starting substances for carrying out the process according to the invention. In this formula (III) the radical R preferably or in particular has the meaning which has already been given above as preferred or as particularly preferred for R in connection with the description of the compounds of the general formula (I). X represents fluorine, chlorine, bromine or iodine, preferably chlorine. The starting substances of the general formula (III) are known and/or can be prepared by processes which are known per se (compare Diversi et. al., Synthesis 1971, 258; U.S. patent application Ser. No. 3674831; Cesare Ferri, "Reaktionen in der organisthen Synthese" ("Reactions in organic synthesis"), 1978, 460–461, Georg Thieme Verlag, Stuttgart).

Possible diluents for carrying out the process according to the invention are all inert organic solvents. These include, preferably, aliphatic, alicyclic or aromatic hydrocarbons, such as, for example, petroleum ether, hexane, heptane, cyclohexane, methylcyclohexane, benzene, toluene, xylene or decalin, preferably toluene or xylene; halogenated hydrocarbons, such as, for example, chlorobenzene, dichlorobenzene, methylene chloride, chloroform, tetrachloromethane, dichloroethane or trichloroethane, preferably chlorobenzene or dichlorobenzene; ethers, such as, for example, diethyl ether, diisopropyl ether, methyl t-butyl ether, methyl t-amyl ether, dioxane, tetrahydrofuran, 1,2-dimethoxyethane, 1,2-diethoxyethane or anisole, preferably 1,2-dimethoxyethane, methyl t-butyl ether or methyl t-amyl ether; and nitriles, such as, for example, acetonitrile, propionitrile, n- or iso-butyronitrile or benzonitrile, preferably acetonitrile, as well as n- or iso-butyronitrile.

The reaction temperatures can be varied within a substantial range in carrying out the process according to the invention. The reaction is in general carried out at temperatures from 60° C. to 180° C., preferably at temperatures from 70° C. to 150° C.

The process according to the invention is in general carried out under normal pressure or reduced pressure. However, it is also possible to carry out the process under increased pressure, but the hydrogen halide formed must be removed by occasionally letting down the apparatus. The process is preferably carded out under normal pressure, and if appropriate an inert gas, such as, for example, nitrogen, is passed through the reaction solution for complete removal of the hydrogen halide formed.

For carrying out the process according to the invention for the preparation of the compounds of the formula (I), in general 1 to 1.3 mol, preferably 1 to 1.2 mol, of the cycloalkanecarboxylic acid derivative of the general formula (III) are employed per mol of the aminophenol of the general formula (II).

In one possible embodiment, the cycloalkanecarboxylic acid derivative of the general formula (III) is initially introduced into the organic solvent and the mixture is heated. The aminophenol of the general formula (II) is then metered in at temperatures between 80° C. and 120° C. If appropriate, the mixture can also be heated to an even higher temperature in order to bring the reaction to completion.

In a preferred embodiment, the aminophenol of the general formula (II) is initially introduced into the organic solvent and the mixture is heated. The cycloalkanecarboxylic acid derivative of the general formula (III) is then metered in at temperatures between 80° C. and 120° C. If appropriate, the mixture can also be heated to an even higher temperature in order to bring the reaction to completion.

The substances prepared according to the invention can be employed against plant pests, in particular phytopathogenic fungi.

PREPARATION EXAMPLES

Example 1

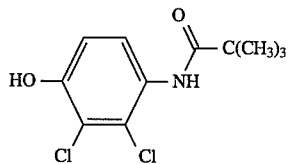

9.3 g (0.05 mol) of 4-amino-2,3-dichlorophenol (purity: 96%) are suspended in 175 ml of toluene and the suspension is heated to 100° C., while stirring. 6.3 g (0.0525 mol) of pivalic chloride are then added dropwise at 100°–105° C. and, when the addition has ended, the mixture is stirred under reflux for a further 4 hours. After the reaction mixture has cooled, the precipitate is filtered off at 0°–10° C. and washed with a little toluene. 12.5 g (95.4% of theory) of pivalic acid (2,3-dichloro-4-hydroxy)-anilide of melting point 62° C. are obtained.

Example 2

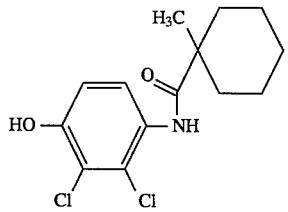

9.3 g (0.05 mol) of 4-amino-2,3-dichlorophenol (purity: 96%) are suspended in 175 ml of toluene and the suspension is heated to 100° C., while stirring. 8.8 g (0.0525 mol) of 1-methylcyclohexane-1-carboxylic acid chloride (purity: 96%) are then added dropwise at 100°–105° C. and, when the addition has ended, the mixture is stirred under reflux for a further 4 hours. After the reaction mixture has cooled, the precipitate is filtered off at 0°–10° C. and washed with a little toluene. 13.95 g (92.3% of theory) of 1-methylcyclohexane-1-carboxylic acid (2,3-dichloro-4-hydroxy)-anilide of melting point 154° C. are obtained.

Example 3

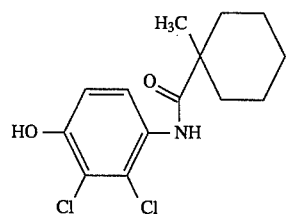

9.3 g (0.05 mol) of 4-amino-2,3-dichlorophenol (content: 96%) are dissolved in 50 ml of 1,2-dimethoxyethane and the solution is heated to 88° C., while stirring. 8.8 g (0.0525 mol) of 1-methylcyclohexane-1-carboxylic acid chloride (purity: 96%) are added dropwise at 100°–105° C. in the come of 20 minutes, and, when the addition has ended, the mixture is stirred under reflux for a further 6 hours. After the reaction mixture has cooled, 1.5 g of 4-amino-2,3-dichlorophenol hydrochloride are filtered off. The filtrate is concentrated and the residue is extracted by stirring with a little toluene and filtered off. 13.95 g of 1-methylcyclohexane-1-carboxylic acid (2,3-dichloro-4-hydroxy)-anilide of melting point 154° C. are obtained. This corresponds to a yield of 90.8% of theory, based on the 4-amino-2,3-dichlorophenol reacted.

We claim:

1. A process for preparing a compound of the formula

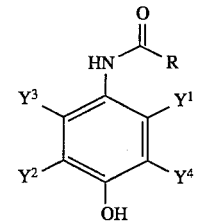

in which

R represents alkyl which is optionally mono- or polysubstituted in an identical or different manner by halogen, or represents cycloalkyl which is optionally mono- or polysubstituted in an identical or different manner by alkyl, halogenoalkyl or halogen and $Y^1$, $Y^2$, $Y^3$, $Y^4$ are identical or different and represent hydrogen, halogen, cyano, in each case optionally halogen-substituted alkyl, alkoxy or alkylthio, which comprises dissolving or forming a suspension of an amino phenol of the formula

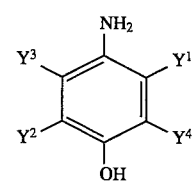

wherein $Y^1$, $Y^2$, $Y^3$ and $Y^4$ have the above-mentioned meanings, in an organic solvent, and reacting the mixture produced above with a carboxylic acid derivative of the formula

in which

R has the above-mentioned meaning, and

X represents halogen, in the absence of a base and in the absence of water at a temperature from 50° to 180° C.

2. The process according to claim 1, wherein

R represents straight-chain or branched alkyl having 1–8 carbon atoms which is optionally mono- to tetrasubstituted in an identical or different manner by halogen, or represents cyclopropyl, cyclobutyl, cyclopentyl, cyclohexyl or cycloheptyl which are in each case optionally mono- to tetrasubstituted in an identical or different manner by halogen, straight-chain or branched halogenoalkyl or alkyl having 1 to 4 carbon atoms, $Y^1$ represents hydrogen, fluorine, chlorine, bromine, cyano, straight-chain or branched alkyl having having 1 to 4 carbon atoms, or in each case straight-chain or branched alkoxy or alkylthio having in each case 1 to 4 carbon atoms, or represents in each case straight-chain or branched halogenoalkyl, halogenoalkoxy or halogenoalkylthio having 1 to 4 carbon atoms and 1 to 5 identical or different halogen atoms, $Y^2$ represents hydrogen, fluorine, chlorine, bromine, cyano, straight-chain or branched alkyl having having 1 to 4 carbon atoms, or in each case straight-chain or branched alkoxy or alkylthio having in each case 1 to 4 carbon atoms, or represents in each case straight-chain or branched halogenoalkyl, halogenoalkoxy or halogenoalkylthio having 1 to 4 carbon atoms and 1 to 5 identical or different halogen atoms, $Y^3$ represents hydrogen, fluorine, chlorine, bromine, cyano, straight-chain or branched alkyl having having 1 to 4 carbon atoms, or in each case straight-chain or branched alkoxy or alkylthio having in each case 1 to 4 carbon atoms, or represents in each case straight-chain or branched halogenoalkyl, halogenoalkoxy or halogenoalkylthio having 1 to 4 carbon atoms and 1 to 5 identical or different halogen atoms, and $Y^4$ represents hydrogen, fluorine, chlorine, bromine, cyano, straight-chain or branched alkyl having having 1 to 4 carbon atoms, or in each case straight-chain or branched alkoxy or alkylthio having in each case 1 to 4 carbon atoms, or represents in each case straight-chain or branched halogenoalkyl, halogenoalkoxy or halogenoalkylthio having 1 to 4 carbon atoms and 1 to 5 identical or different halogen atoms.

3. The process according to claim 1, wherein the reaction temperature is from 60° C. to 180° C.

4. The process according to claim 1, wherein 1 to 1.3 mol of the compound of the formula III per mol of the compound of formula II are employed.

5. The process according to claim 1, wherein X is chlorine.

* * * * *